United States Patent
Vogel et al.

(10) Patent No.: US 6,335,028 B1
(45) Date of Patent: Jan. 1, 2002

(54) IMPLANTABLE PARTICLES FOR URINARY INCONTINENCE

(75) Inventors: Jean Marie Vogel, Boxborough; Richard Thomas, Elmont, both of MA (US); Egisto Boschetti, Croissy sur Seine (FR)

(73) Assignee: Biosphere Medical, Inc., Rockland, MA (US)

(*) Notice: Subject to any disclaimer, the term of this patent is extended or adjusted under 35 U.S.C. 154(b) by 0 days.

(21) Appl. No.: 09/263,773

(22) Filed: Mar. 5, 1999

Related U.S. Application Data

(60) Provisional application No. 60/077,166, filed on Mar. 6, 1998.

(51) Int. Cl.$^7$ .............................. A61K 9/16; A61K 9/18
(52) U.S. Cl. ..................... 424/422; 424/423; 424/489; 424/1.11
(58) Field of Search ................ 424/422, 423, 424/489, 1.11

(56) References Cited

U.S. PATENT DOCUMENTS

| | | | |
|---|---|---|---|
| 3,919,411 A | 11/1975 | Glass et al. | 424/81 |
| 4,197,846 A | 4/1980 | Bucalo | 128/218 P |
| 4,413,070 A | 11/1983 | Rembaum | 523/223 |
| 4,452,916 A | 6/1984 | Boschetti | 521/38 |
| 4,500,658 A | 2/1985 | Fox | 523/117 |
| 4,525,358 A | 6/1985 | Baltes et al. | 514/255 |
| 4,622,362 A | 11/1986 | Rembaum | 525/54.1 |
| 4,786,555 A | 11/1988 | Howard, Jr. | 428/403 |
| 4,803,075 A | 2/1989 | Wallace et al. | 424/423 |
| 5,007,940 A | 4/1991 | Berg | 623/66 |
| 5,344,452 A | 9/1994 | Lemperle | 623/11 |
| 5,451,406 A | 9/1995 | Lawin | 424/423 |
| 5,470,911 A | 11/1995 | Rhee et al. | 525/54.1 |
| 5,550,188 A | 8/1996 | Rhee et al. | 525/54.1 |
| 5,578,709 A | 11/1996 | Woiszwillo | 530/410 |
| 5,633,001 A | 5/1997 | Ågerup | 424/423 |
| 5,635,215 A | 6/1997 | Boschetti et al. | 424/501 |
| 5,648,100 A | 7/1997 | Boschetti et al. | 424/501 |
| 5,792,478 A | * 8/1998 | Lawin et al. | 424/502 |

FOREIGN PATENT DOCUMENTS

| | | |
|---|---|---|
| EP | 0 648 480 A2 | 4/1995 |
| FR | 2378808 | 8/1978 |
| WO | WO 92/21327 | 12/1992 |

OTHER PUBLICATIONS

Krukowski, et al., "Charged Beads Stimulate Bone Formation" 34$^{th}$ Annual Meeting Orth. Res. Soc. Feb. 1988.

E. Boschetti, Microspheres for Biochromatography and Biomedical Applications; Part 1, Preparation of Microbeads In: Microspheres, Microencapsulation and Liposomes, John Wiley & Sons, Arshady R., Ed. 2: 171–189 (1999).

Mazza et al., "Polymer Design in Dye Chromatography: From the definition of monomers to the evaluation of polymeric supports," in Protein–Dye Interactions: Developments and Applications, Vijayalakshmi M.A. ed., Elsevier Appl. Sciences, Elsevier Sci. Publ. Ltd., pp. 126–136 (1989).

Horák D. et al., "Hydrogels in Endovascular Embolization. I. Spherical Particles of Poly(2–hydroxyethyl methacrylate) and Their Medico–biological Properties," *Biomaterials*, 7:188–192 (1986).

Horák D. et al., "Hydrogels in Endovascular Embolization. II. Clinical Use of Spherical Particles," *Biomaterials*, 7:467–470 (1986).

(List continued on next page.)

Primary Examiner—Thurman K. Page
Assistant Examiner—H. Sheikh
(74) Attorney, Agent, or Firm—Pennie & Edmonds LLP

(57) ABSTRACT

The invention encompasses the treatment of urinary incontinence, gastroesophageal reflux disease and the amelioration of skin wrinkles using biocompatible hydrophilic cationic microparticles and a cell adhesion promoter.

21 Claims, 1 Drawing Sheet

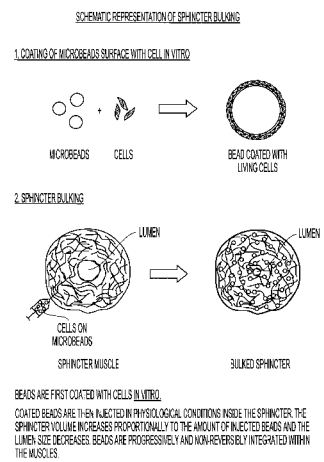

OTHER PUBLICATIONS

Horák D. et al., "Hydrogels in Endovascular Embolization. III. Radiopaque Spherical Particles, Their Preparation and Properties," *Biomaterials*, 8:142–144 (1987).

Berman C.J. et al., "Comparative Cost Analysis of Collagen Injection And Fascia Lata Sling Cystourethropexy For The Treatment of Type III Incontinence in Women," *J. Urology*, 157:122–124 (1997).

Boschetti E., "Polyacrylamide Derivatives To The Service Of Bioseparations," *J. Biochem–Biophys. Meth.*, 19:21–36 (1989).

Boschetti E. et al., "Synthese et copolymerisation de nouveaux monomeres acryliques diiodes et triiodes," *Bull. Soc. Chim.Fr.*, 4:669–677 (1996).

Cherksey B.D. et al., "Adrenal Chromaffin Cells on Microcarriers Exhibit Enhanced Long–Term Functional Effects When Implanted into the Mammalian Brain," *IBRO*, 657–664 (1996).

Chowdhury R. et al., In: Advanced Research on Animal Cell Technology, A.O.A. Miller ed., Kluwers Acad. Press, 315–327 (1989).

Eppley B. L. et al., "A Potential Biomaterial Composite for Dermal and Subcutaneous Augmentation," *Annals of Plastic Surgery*, 32(5):463–468 (1994).

Herschorn S. et al., "Followup Of Intraurethal Collagen For Female Stress Urinary Incontinence," *J. Urology*, 156:1305–1309 (1996).

Herzo et al., "Urinary Incontinence: Medical and Psychosocial Aspects," *Ann. Rev. Gerontol. Geriatrics*, 9(Chap. 3):74–119 (1989).

Johnson W.E. et al., "Outcome of Respiratory Symptons After Anti–reflux Surgery on Patients With Gastroesphageal Reflux Disease," *Archives of Surgery*, 131:489–492 (1996).

Khullar V. et al., "GAX Collagen In The Treatment of Urinary Incontinence In Elderly Women: A Two Year Follow Up," *British J. Obstetrics & Gynecology*, 104:96–99 (1996).

Klutke C.G. et al., "Early Results With Antegrade Collagen Injection for Post–Radical Prostatectomy Stress Urinary Incontinence," *J. Urology*, 156:1703–1706 (1996).

Kondo A. et al., "Bladder Neck Support Prosthesis: A Nonoperative Treatment For Stress Or Mixed Urinary Incontinence," *J. Urology*, 157:824–827 (1996).

Laurent A. et al., "Trisacryl Gelatin Microspheres For Therapeutic Embolization, I: Development and In Vitro Evaluation," *Am. J. Neuroradiol.*, 17:533–540 (1996).

Leonard M.P. et al., "Treatment of Urinary Incontinence In Children By Endoscopically Directed Bladder Neck Infection of Collagen," *J. Urology*, 156:637–641 (1996).

Levesque P.E. et al., "Ten–Year Experience With The Artificial Urinary Sphincter In Children," *J. Urology*, 156:625–628 (1996).

Levine D.W. et al., "Microcarrier Cell Culture: New Methods for Research–Scale Application," *Somatic Cell Genetics*, 3:149–155 (1977).

Lima S.V.C. et al., "Combined use of enterocystoplasty and a new type of artificial sphincter in the treatment of urinary incontinence," *J. Urology* 156:622–624 (1996).

McClelland M. and Delustro F., "Evaluation of Antibody Class In Response to Bovine Collagen Treatment In Patients With Urinary Incontinence," *J. Urology* 155:2068–2073 (1996).

Nebel O.T. et al., "Symptomatic Gastroesophageal Reflux: Incidence and Precipitating Factors," *Am. J. Dig. Dis.*, 21,(11):953–956 (1976).

Obrenovitch A. et al., "Microcarrier Culture Of Fibroblastic Cells On Modified Trisacryl Beads," *Biol. Cell.*, 46:249–256 (1983).

Perez L.M. et al., "Submucosal Bladder Neck Injection of Bovine Dermal Collagen For Stress Urinary Incontinence In The Pediatric Population," *J. Urology*, 156:633–636 (1996).

Remacle, C. et al., "Cultures of Preadipocytes on Microparticles Their Properties of Adhesion Proliferation and Differentation," Manuscript from University Catholique de Louvain, Laboratiore de Biologie Cellulaire, 1–33.

Reynolds J.C., "Influence of pathophysiology, severity, and cost on the medical management of gastroesophageal reflux disease," *Am. J. Health–Sys. Pharm.* 53:S5–S12 (1996).

van Wezel, A.L., "Growth Of Cell–strains And Primary Cells On Micro–carriers In Homogeneous Culture," *Nature*, 216:64–65 (1967).

A.J. Wein, "Pharmacology of Incontinence," *Urol. Clin. N. Am.*, 22:557–573 (1995).

\* cited by examiner

SCHEMATIC REPRESENTATION OF SPHINCTER BULKING

1. COATING OF MICROBEADS SURFACE WITH CELL IN VITRO

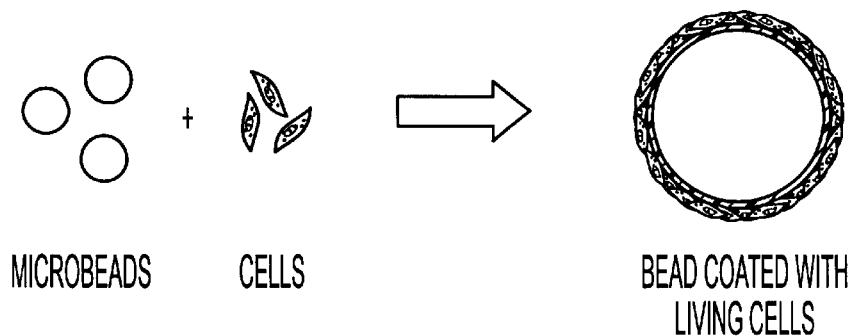

2. SPHINCTER BULKING

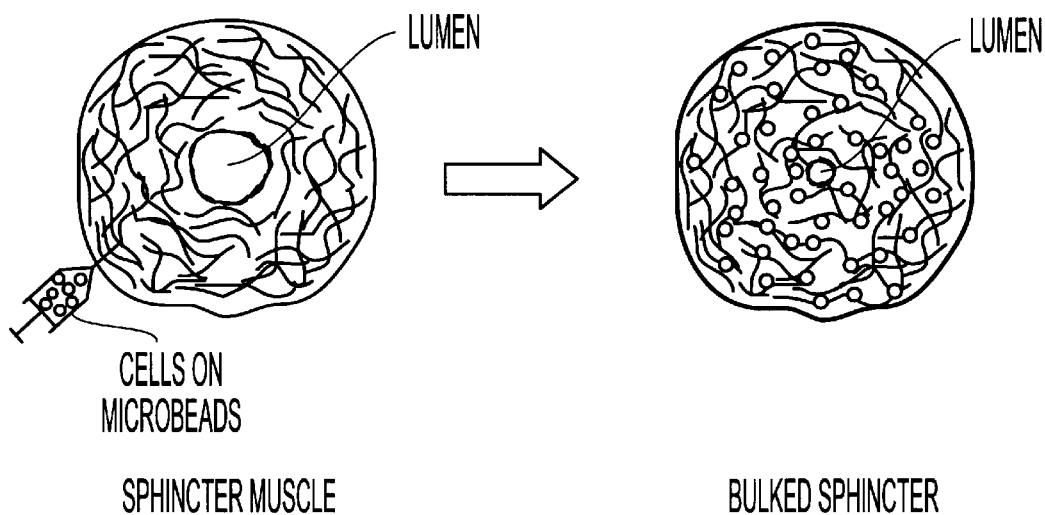

BEADS ARE FIRST COATED WITH CELLS <u>IN VITRO.</u>

COATED BEADS ARE THEN INJECTED IN PHYSIOLOGICAL CONDITIONS INSIDE THE SPHINCTER. THE SPHINCTER VOLUME INCREASES PROPORTIONALLY TO THE AMOUNT OF INJECTED BEADS AND THE LUMEN SIZE DECREASES. BEADS ARE PROGRESSIVELY AND NON-REVERSIBLY INTEGRATED WITHIN THE MUSCLES.

*Fig. 1*

IMPLANTABLE PARTICLES FOR URINARY INCONTINENCE

CROSS-REFERENCE TO RELATED APPLICATIONS

This application is a continuation of co-pending application Ser. No. 60/077,166, filed Mar. 6, 1998.

1. FIELD OF INVENTION

The present invention relates to tissue bulking, the treatment gastroesophageal reflux disease, urinary incontinence and the amelioration of skin wrinkles.

2. BACKGROUND OF INVENTION

2.1 Gastroesophageal Reflux Disease ("GERD")

Although gastroesophageal reflux is a normal physiological phenomenon, in some cases it is a pathophysiological situation that can result in a variety of symptoms which may become severe in extreme cases. Gastro-Esophageal Reflux Disease ("GERD"), describes a backflow of acidic and enzymatic liquid from the stomach to the esophagus. It causes burning sensations behind the sternum that may be accompanied by regurgitation of gastric acid into the mouth or even the lung. Complications of GERD which define the severity of the disease include esophageal tissue erosion, and esophageal ulcer wherein normal epithelium is replaced by a pathological tissue.

Statistical data indicate that about 35% of the American population suffer from heartburn at least once a month and between 5 to 10% once a day. More importantly for this kind of disease about 2% of the American population suffer from GERD based on medical evidence data from endoscopic examination. This disease is related to the age of individuals and seems to increase after 40 years of age. (Nebel O. T. et al., *Am. J. Dig. Dis.*, 21(11):953–956 (1976)).

In normal patients, after a meal the lower esophageal sphincter remains closed, but in patients with GERD, it relaxes and allows some acidic material to reflux into the esophageal tube as a result of stomach contractions. Actually GERD can be attributed primarily to transient relaxation of the lower esophageal sphincter. In other cases, GERD can be attributed to decreased resting tone of the lower esophageal sphincter or to congenital small dimension of the sphincter itself. Other causes also exist which contribute to varying degrees to the existence and severity of this disease.

In addition, there are external factors that contribute to exacerbate the symptoms of GERD, which conditions include eating fatty foods, caffeine intake, smoking, tight clothing and certain medications. Decrease in salivation can also be a factor that exacerbates GERD, since under normal conditions saliva, which is an alkaline liquid, aids in neutralizing acidic reflux and therefore diminishing the duration of the acidic exposure of the esophagus.

Erythema is one of the first visible signs of GERD, which can be seen by endoscopy. Tissue erosion indicates more advanced disease which can then become deep ulcers and lead to cancer (adenocarcinoma increases in incidence faster than other types of cancer). Diffuse ulceration and specific complications occur in about 3.5% of patients less than 65 years of age with esophageal obstruction, blood loss, and in some cases, perforation. Ulcerative situations not only lead to complications, but they are also more resistant to treatments. Although severe complications are uncommon in young patients, they occur in about 20–30% of patients over 65 (Reynolds J. C, *Am. J. Health-Sys. Pharm* 53, (1996)).

Prior to the present invention, in an attempt to increase the function of the sphincter, bulking methods using bovine collagen and Teflon paste have been used in patients. Both methods have been unsuccessful, however, as these materials migrate over time from the initial site of implantation.

At present, GERD is generally managed by over-the-counter ("OTC") antacids or prescription drugs, including proton pump inhibitors, motility agents and $H_2$ blockers. In addition, a portion of GERD patients require surgical intervention; the most common type of surgery is fundoplication which can be done by conventional surgical techniques, or using laparoscopic techniques. However, fundoplication surgery carries the risk of serious side effects and is only marginally successful in curing GERD. Respiratory symptoms are also associated with GERD in about 50% of patients, and in patients undergoing fundoplication, these respiratory symptoms can even increase (76% reported in a study by Johnson W. E. et al., *Archives of Surgery*, 131:489–492 (1996)).

2.2 Urinary Incontinence

Urinary incontinence is a prevalent problem that affects people of all ages and levels of physical health, both in the community at large and in healthcare settings. Medically, urinary incontinence predisposes a patient to urinary tract infections, pressure ulcers, perineal rashes, and urosepsis. Socially and psychologically, urinary incontinence is associated with embarrassment, social stigmatization, depression, and especially for the elderly, an increased risk of institutionalization (Herzo et al., *Ann. Rev. Gerontol. Geriatrics*, 9:74 (1989)). Economically, the costs are astounding; in the United States alone, over ten billion dollars per year is spent managing incontinence.

Incontinence can be attributed to genuine urinary stress (urethra hypermobility), to intrinsic sphincter deficiency ("ISD"), or both. It is especially prevalent in women, and to a lesser extent incontinence is present in children (in particular, ISD), and in men following radical prostatectomy.

One approach for treatment of urinary incontinence involves administration of drugs with bladder relaxant properties, with anticholinergic medications representing the mainstay of such drugs. For example, anticholinergics such as propantheline bromide, and combination smooth muscle relaxant/anticholinergics such as racemic oxybutynin and dicyclomin, have been used to treat urge incontinence. (See, e.g., A. J. Wein, *Urol. Clin. N. Am.*, 22:557 (1995)). Often, however, such drug therapies do not achieve complete success with all classes of incontinent patients, and often results in the patient experiencing significant side effects.

Besides drug therapies, other options used by the skilled artisan prior to the present invention include the use of artificial sphincters (Lima S. V. C. et al., *J. Urology*, 156:622–624 (1996), Levesque P. E. et al., *J. Urology*, 156:625–628 (1996)), bladder neck support prosthesis (Kondo A. et al., *J. Urology*, 157:824–827 (1996)), injection of crosslinked collagen (Berman C. J. et al., *J. Urology*, 157:122–124 (1997), Perez L. M. et al., *J. Urology*, 156:633–636 (1996); Leonard M. P. et al., *J. Urology*, 156:637–640 (1996)), and injection of polytetrafluoroethylene (Perez L. M. et al., *J. Urology*, 156:633–636 (1996)).

A recent well known approach for the treatment of urinary incontinence associated with ISD is to subject the patient to periurethral endoscopic collagen injections. This augments the bladder muscle in an effort to reduce the likelihood of bladder leakage or stress incontinence.

Existing solutions to circumvent incontinence have well known drawbacks. The use of artificial sphincters for children with intractable incontinence requires long term surveillance of the urinary tract because of the potential for renal failure after device placement (Levesque P. E. et al., *J. Urology*, 156:625–628 (1996)). While endoscopically directed injections of collagen around the bladder neck has a quite high success rate in sphincter deficiency with no significant morbidity, the use of collagen can result in failures that occur after an average of two years and considerations need to be given to its cost effectiveness (Khullar V. et al., *British J. Obstetrics & Gynecology*, 104:96–99 (1996)). In addition, deterioration of patient continency, probably due to the migration phenomena (Perez L. M. et al.) may require repeated injections in order to restore continency (Herschorn S. et al., *J. Urology*, 156:1305–1309 (1996)).

The results with using collagen following radical prostatectomy for the treatment of stress urinary incontinence have also been generally disappointing (Klutke C. G. et al., *J. Urology*, 156:1703–1706 (1996)). Moreover, one study provides evidence that the injection of bovine dermal collagen produced specific antibodies of IgG and IgA class. (McCell and, M. and Delustro, F., *J. Urology* 155, 2068–2073 (1996)). Thus, possible patient sensitization to the collagen could be expected over the time.

Despite of the limited success rate, transurethral collagen injection therapy remains an acceptable treatment for intrinsic sphincter deficiency, due to the lack other suitable alternatives.

2.3 Skin Wrinkles

Damage to the skin due to aging or exposure to the sun and other elements often results in wrinkles and other skin anomalies. In order to remove wrinkles from the skin, people often resort to cosmetic surgery, such as face lifts and skin tucks. In addition, collagen injections have been used to remove or ameliorate skin wrinkles. Collagen injections have also been used for tissue bulking or to increase the fullness of certain body parts, e.g., to increase the fullness of lips or around the eyes and eyebrow area of the face. However, collagen is a naturally occurring substance which the body may enzymatically degrade and eliminate over time, thus requiring repeat treatments. Even more alarming from a cosmetic perspective, collagen may move from the initial site of injection, causing unsightly bumps and bulges under the skin at undesired locations.

Microbeads or solid microparticles have been used for the correction of skin wrinkles. For examples, silicone particles, TEFLON paste, collagen beads and polyacrylic microspheres have been used with disappointing results due to, inter alia, adverse tissue reactions, biological degradation and migration from the initial implantation location.

2.4 MicroParticles

Prior to the present invention, microspheres have been manufactured and marketed for in vitro use in anchorage dependent cell culture. (Van Vezel, A. L., *Nature*, 216:64–65 (1967); Levine et al., *Somatic Cell Genetics*, 3:149–155 (1977); Obrenovitch et al., *Biol. Cell.*, 46:249–256 (1983)). They have also been used in vivo to occlude blood vessels in the treatment of arteriovascular malformation, fistulas and tumors (See, U.S. Pat. No. 5,635,215, issued Jun. 3, 1997 to Boschetti et al.; Laurent et al., *J. Am. Soc. Neuroiol*, 17:533–540 (1996); and Beaujeux et al. *J. Am. Soc. Neuroial*, A:533–540 (1996)).

Further, direct implantation of cells into living tissues such as brain or liver to correct specific deficiencies has been attempted albeit with a number of failures. The major problems associated with direct cell transplantation are the long term viability of the cell transplant and the immunopathological as well as histological responses. Microparticles with cells attached on their surface have been used in some in vivo applications. Cherkesey et al., IBRO, 657–664 (1996), described the culture of adrenal cells on coated dextran beads and the implantation into mammalian brain to supplant some specific disorders related to 6-hydroxydopamine-induced unilateral lesions of the substantia nigra. The pre-attachment of cells to dextran microcarriers allowed for improved functions of the cells implanted into the brain. Also liver cells transplantation has been used to manage acute liver failure, or for the replacement of specific deficient functions such as conjugation of bilirubin or synthesis of albumin. For this purpose, an intrasplenic injection of hepatocytes grown on the surface of microspheres was performed (Roy Chowdhury et al., in: Advanced Research on Animal Cell Technology, AOA Miller ed., 315–327, Kluers Acad. Press, 1989).

Most of cell implant results have been, however, largely disappointing for the designated functions (or have had low levels of biological function).

3. SUMMARY OF INVENTION

The present invention encompasses the use of implantable microparticles in the treatment of GERD, urinary incontinence and skin wrinkles. In each use the particles are implanted into the appropriate tissue, muscle, organ etc. as a bulking agent. Further, in each use the microparticles are preferably pre-coated, with autologous cells, for example, muscle cells, fat cells and the like. The microparticles of the invention are biocompatible non-toxic polymers coated with, linked to or filled with cell adhesion promoters. The microparticles preferably contain a positive charge on their surface by way of a cationic monomer or polymer.

In one embodiment, the invention encompasses the treatment of gastroesophageal reflux disease in a human which comprises implanting hydrophilic biocompatible microparticles comprising (a) a positive charge and a cell adhesion promoter; and (b) autologous cells layered on the surface of said beads, into the lower esophageal sphincter. The microparticles are preferably microspheres or microbeads which are described in detail herein. The autologous cells are preferably taken from the area where the implantation is to be made. Serum or whole blood taken from the patient can be used to wash the microparticles prior to implantation. For GERD treatment implantation may also be made by using standard techniques known to the skilled artisan, such as injection (or injections) via syringe or other suitable devices.

In yet another embodiment, the invention encompasses the treatment of urinary incontinence in a human which comprises implanting hydrophilic biocompatible microparticles comprising (a) a positive charge and a cell adhesion promoter; and (b) autologous cells layered on the surface of the beads, into the urinary sphincter. The microparticles are preferably microspheres or microbeads as described herein. Further, the autologous cells are preferably taken from the area where the implantation is to be made. Serum or whole blood from the patient can be used to wash the microparticles prior to implantation. Implantation is generally made using a syringe or other device suitable for the particular tissue of implantation.

In another embodiment, the invention encompasses a method of treating skin wrinkles in a human which comprises the administration or implantation of microparticles comprising a hydrophilic copolymer having a positive charge, and a cell adhesion promoter, which microparticles have been pre-treated with autologous cells. The microparticles can be simply exposed to the autologous cells or mixed thoroughly with autologous cells prior to implantation.

It should be recognized that both treatments for GERD and urinary incontinence described above can be used in combination with conventional therapies now used to treat these diseases i.e., oral diuretics, antacids, suitable drug therapy and the like. Such combination therapy can lead to a faster, safer and more comfortable recovery for the patient.

In yet another embodiment, the invention encompasses the treatment or amelioration of skin wrinkles which comprises administering hydrophilic biocompatible microparticles comprising: (a) a positive charge and a cell adhesion promoter; and (b) autologous cells, collagen, collagen derivatives or glucosaminoglycans layered on the surface of the beads, into the area of or surrounding the skin wrinkles. In other words, microspheres or microbeads coated with a cell adhesion promoter and pre-treated with the appropriate tissue bulking cells, are administered to the area of treatment.

As used herein the terms "administered", "implanted", or "implantation" are used interchangeably and mean that the material is delivered to the area of treatment by techniques know to those skilled in the art and appropriate for the disease to be treated. Both invasive and non-invasive methods may be used for delivery.

4. BRIEF DESCRIPTION OF THE DRAWINGS

FIG. 1 is a schematic representation of sphincter bulking. Beads are coated and injected under physiological conditions into the sphincter. The sphincter volume increases proportionally to the amount of injected beads and the lumen size decreases. The beads are progressively and non-reversibly integrated within the muscles.

5. DETAILED DESCRIPTION OF THE INVENTION

The present invention uses microparticles, particularly microbeads, having a positive charge on its surface and a cell adhesion promoter and optionally, a cell growth promoting agent, to treat GERD, urinary incontinence, and skin wrinkles. The microparticles of the invention are preferably used with autologous cells. In other words, the microparticles of the invention are colonized with the appropriate cells prior to implantation. This pre-implantation step has been shown to reduce or eliminate immunological responses and implantation rejection reactions. Further, the use of non-biodegradable biologically compatible microbeads with positive charges and autologous cells, whether tissue-specific or not, improves tissue acceptance and overall treatment.

According to the methods of the present invention, treatment of GERD, urinary incontinence, and skin wrinkles is achievable while avoiding or substantially reducing adverse tissue reactions, including implantation rejection, degradation of particles, resorption, migration and other adverse events. The methods of the invention also involve increased connective tissue response.

Microbeads or microparticles for use in the present invention are based on a biocompatible non-toxic polymer coated with agents which promote cell adhesion. Living cells attach to the microparticles forming layered cells therein which link with surrounding tissues to enhance long term stability of the beads.

Microparticles intended to be implanted in various locations of the body according to the present invention are composed of a non-resorbable hydrophilic polymer containing the appropriate material for cell adhesion, and may additionally contain radiopaque molecules or other marking agents, to facilitate localization by radiology prior to or during intervention. Hydrophilic copolymers usable for this application are those of the acrylic family such as polyacrylamides and their derivatives, polyacrylates and their derivatives as well as polyallyl and polyvinyl compounds. All of these polymers are crosslinked so as to be stable and non-resorbable, and can contain within their structure other chemicals displaying particular properties, such as chemotactic effects, promotion of cell adhesion to cells or tissues, such as cells of the esophagus wall or the urethra wall, or skin cells, and/or marking agents.

The microparticles for use in the present invention are non-toxic to tissues and cells, biocompatible, and adhesive to various cells and tissues at the site of implantation by means of the cell growth they promote. In addition, these microparticles are non-resorbable and non-biodegradable, and thus are stable, durable, and will maintain their general shape and position once implanted at a desired site.

In general, microparticles for use in the present invention may have any shape, with microparticles which are spherical in shape being preferred. Microparticles for use in the present invention may have diameters ranging between about 10 $\mu$m to about 1000 $\mu$m. Preferably, microparticles for use in the present invention which have cells adhered to the surface thereof will have diameters ranging between 50 $\mu$m and 1000 $\mu$m.

Possible variations of the present invention include replacing the microparticles with any biocompatible, non-toxic non-resorbable polymeric particles, membrane, fibers or other solid substrates treated with an agent promoting cell adhesion. The invention also includes linear soluble polymers which, after injection, crosslink in situ to constitute a solid, cell adhesion promoting filling agent. Preparation and/or injection of empty microparticles (microbubbles) that are prepared in advance or are generated in place via the use of appropriate catheters, are also contemplated in this invention.

The microparticles, or other solid substrates, for use in the present invention are flexible, such that they can easily pass into and through injection devices and small catheters without being permanently altered, but the microparticles are also resistant to the muscle contraction stress generated during and after the implantation process. They are also thermally stable which allows for easy, convenient sterilization, and frozen storage.

The microparticles, or other solid substrates, for use in the present invention are also stable in suspension which allows the microparticles or other solid substrates to be formulated and stored in suspension and injected with different liquids. More specifically, the hydrophilic nature of the microparticles permits placing them in suspension, and in particular, in the form of sterile and pyrogenic (pyrogen-free) injectable solutions, while avoiding the formation of aggregates or adhesion to the walls of storage containers and implantation devices, such as catheters, syringes, needles, and the like. Preferably, these injectable solutions contain microparticles or other solid substrates distributed approximately in caliber segments ranging between about 10 $\mu$m and about 2000 $\mu$m.

The microparticles of the present invention are both hydrophilic and cationic. The microparticles preferably comprise a copolymer of a neutral hydrophilic monomer, a difunctional monomer, one or more monomers having a cationic charge, and optionally, a functionalized monomer capable of rendering the microparticle detectable. The microparticles may also comprise one or more cell adhesion promoters and a marking agent.

The copolymer is preferably a hydrophilic acrylic copolymer which comprises in copolymerized form about 25 to about 98% neutral hydrophilic acrylic monomer by weight, about 2 to about 50% difunctional monomer by weight and about 0 to about 50% by weight of one or more monomers having a cationic charge.

By way of example, the copolymers described in French Patent 2,378,808, which is incorporated herein by reference, can be used in accordance with this invention to prepare the base microparticle copolymer.

As hydrophilic acrylic monomer, acrylamide and its derivatives, methacrylamide and its derivatives or hydroxymethylmethacrylate can be used.

Examples of difunctional monomer, include but are not limited to the N,N'-methylene-bis-acrylamide, N',N'-diallyltartiamide or glyoxal-bis-acrylamide.

Further, the monomer having a cationic charge, includes but is not limited to those carrying a tertiary or quaternary amine function, preferably diethylaminoethyl acrylamide, methacrylamidopropyl trimethylammonium or acrylamidoethyl triethylammonium.

In a particularly preferred embodiment, a copolymer comprising about 25 to about 98% methacrylamide by weight, about 2 to about 50% N,N-methylene-bis-acrylamide by weight is used.

In one particularly advantageous embodiment of the invention, it is possible to increase the stability of the microspheres by reticulating the adhesion agent. By way of example, in the case of gelatin, the reticulating agent can be chosen among the difunctional chemical agents reacting on the gelatin amines (e.g., glutaraldehyde, formaldehyde, glyoxal, and the like).

The functionalized monomer is generally obtained by chemical coupling of the monomer with a marker, which can be:

- a chemical dye, such as Cibacron Blue or Procion Red HE-3B, making possible a direct visualization of the microspheres (Boschetti, *J. Biochem-Biophys. Meth.*, 19:21–36 (1989)). Examples of functionalized monomer usable for this type of marking N-acryloyl hexamethylene Cibacrone Blue or N-acryloyl hexamethylene Procion Red HE-3B;
- a magnetic resonance imaging agent (erbium, gadolinium or magnetite);
- a contrasting agent, such as barium or iodine salts, including for example acylamino-e-propion-amido)-3-triiodo-2, 4, 6-benzoic acid, which can be prepared under the conditions described by Boschetti et al. (*Bull. Soc. Chim.*, No. 4 *France*, (1986)). In the case of barium or magnetite salts, they can be directly introduced in powered form in the initial monomer solution.

As indicated above it is also possible to mark the microspheres after their synthesis. This can be done, for example, by grafting of fluorescent markers derivatives (including for example fluorescein isothiocyanate (FITC), rhodamine isothiocyanate (RITC) and the like).

Various types of cell adhesion promoters well known in the art may be used in the present invention. In particular, cell adhesion promoters can be selected from collagen, gelatin, glucosaminoglycans, fibronectins, lectins, polycations (such polylysine, chitosan and the like), or any other natural or synthetic biological cell adhesion agent.

Preferably, the cell adhesion promoter is present in the microparticle, or other solid substrate, in an amount between about 0.1 to 1 g per ml of settled microparticles.

Microparticles are prepared by suspension polymerization, drop-by-drop polymerization or any other method known to the skilled artisan. The mode of microparticle preparation selected will usually depend upon the desired characteristics, such as microparticle diameter and chemical composition, for the resulting microparticles. The microparticles of the present invention can be made by standard methods of polymerization described in the art (see, e.g., E. Boschetti, *Microspheres for Biochromatography and Biomedical Applications. Part I, Preparation of Microbands* In: Microspheres, Microencapsulation and Liposomes, John Wiley & Sons, Arshady R., Ed., 1998 (in press) which is incorporated herein by reference). Microspheres are prepared starting from an aqueous solution of monomers containing adhesion agents such as collagen (gelatin is a denatured collagen). The solution is then mixed with a non-aqueous-compatible solvent to create a suspension of droplets, which are then turned into solid gel by polymerization of monomers by means of appropriate catalysts. Microspheres are then collected by filtration or centrifugation and washed.

Cell adhesion promoters or marking agents are introduced on microbeads by chemical coupling procedures well known in affinity chromatography, referred to by the term "ligand immobilization". Another method of introduction is by diffusion within the gel network that constitutes the bead and then trapping the diffused molecules in place by precipitation or chemical cross-linking. Therapeutic agents, drugs or any other active molecules that are suitable for transportation by the beads can also be introduced into the microbeads prior to bead implantation according to this last method.

The microspheres of the invention can also be obtained by standard methods of polymerization described in the art such as French Patent 2,378,808 and U.S. Pat. No. 5,648,100, each of which is incorporated herein by reference. In general, the polymerization of monomers in solution is carried out at a temperature ranging between about 0° C. and about 100° C. and between about 40° C. and about 60° C., in the presence of a polymerization reaction initiator.

The polymerization initiator is advantageously chosen among the redox systems. Notably, it is possible to use combinations of an alkali metal persulfate with N,N,N',N'-tetramethylethylenediamine or with dimethylaminopropionitrile, organic peroxides such as benzoyl peroxides or even 2,2'-azo-bis-isobutyronitrile.

The quantity of initiator used is adapted by one skilled in the art to the quantity of monomers and the rate of polymerization sought.

Polymerization can be carried out in mass or in emulsion.

In the case of a mass polymerization, the aqueous solution containing the different dissolved constituents and the initiator undergoes polymerization in an homogeneous medium. This makes it possible to access a lump of aqueous gel which can then be separated into microspheres, by passing, for example, through the mesh of a screen.

Emulsion or suspension polymerization is the preferred method of preparation, since it makes it possible to access directly microspheres of a desired size. It can be conducted as follows: The aqueous solution containing the different dissolved constituents (e.g., different monomers, cell adhesion agent), is mixed by stirring, with a liquid organic phase which is not miscible in water, and optionally in the presence of an emulsifier. The rate of stirring is adjusted so as to obtain an aqueous phase emulsion in the organic phase forming drops of desired diameter. Polymerization is then started off by addition of the initiator. It is accompanied by an exothermic reaction and its development can then be followed by measuring the temperature of the reaction medium.

It is possible to use as organic phase vegetable or mineral oils, certain petroleum distillation products, chlorinated hydrocarbons or a mixture of these different solutions. Furthermore, when the polymerization initiator includes several components (redox system), it is possible to add one of them in the aqueous phase before emulsification.

The microspheres thus obtained can then be recovered by cooling, decanting and filtration. They are then separated by size category and washed to eliminate any trace of secondary product.

The polymerization stage can be followed by a stage of reticulation of the cell adhesion agent and possibly by a marking agent stage in the case of microspheres rendered identifiable by grafting after synthesis.

Microparticles of the present invention which have the specific properties of cell adhesion and growth promotion can be used directly for tissue bulking. Moreover, the microparticles of the present invention can have specific autologous cells grown on their surface in vitro, thereby making the microparticles particularly useful for tissue bulking.

Prior to the present invention, the injection of implantable substances suspended in a physiological solution into a tissue resulted in the formation of discrete aggregates inside the muscle mass. These discrete aggregates can constitute various amounts of the implanted substance which stays together, however, the substance does not become attached to or a part of the tissue itself. This detachment allows the implanted substance to move from the original implantation site.

According to the present invention, in order to avoid this problem, the microparticles may be injected individually and separately, or more preferably, the surface of the microparticles may be colonized by a layer of cells for better integration and long term stability of the implant.

Microparticles of the present invention demonstrate superior ability to grow cells on their surfaces. For example, primary muscle cells have been successfully adhered to the surface of the microparticles of the present invention thereby allowing for a better integration within a muscle tissue. In addition, since the ultimate goal of tissue bulking is to artificially increase tissue mass, preadipocytes have also been used to colonize the surface of the microparticles prior injection. In this case, the preadipocytes have a volume similar to any other regular cell, but after implantation when the preadipocytes are subject to in vivo physiological conditions, they accumulate droplets of fats thereby increasing the mass of the implant by more than 10% in volume.

According to the present invention, one means of performing tissue bulking in a patient can be described as follows:

a) Primary cells are extracted from the patient by a simple biopsy and isolated;
b) These cells are grown on the surface of the microparticles under growth promoting conditions (e.g., possibly using a nutrient media which contains autologous serum (drawn from the patient), until confluence);
c) the microparticles having the patient's cells grown on the top are injected into the patient's target tissue to be bulked.

For the treatment of GERD, the microparticles, or other solid substrates, are introduced via the esophagus, either by endoscopic delivery or by laparoscopic technique, and are injected into the walls of the sphincter where the esophagus meets the stomach, i.e., the lower esophageal sphincter. This decreases the internal lumen of the sphincter muscle thus permitting easier contraction of the muscle with reduced regurgitation of the gastric fluids into the esophagus. In addition, this treatment reduces the inflammation of the lower esophagus. The microparticles, or other solid substrates, may also be loaded with X-ray opaque dye or other imaging agents for subsequent X-ray visualization.

In another embodiment, microparticles injected into the sphincter at the junction of the esophagus and stomach in order to treat GERD may also include an amount of a drug used to treat GERD, such as $H_2$ histamine antagonists including cimetidine, ranitidine, famotidine and nizatidine; inhibitors of $H^+$, $K^+$-ATPase including omeprazole and lansoprazole; antacids including e.g., $Al(OH)_3$, $Mg(OH)_2$, and $CaCO_3$. As with the treatment of urinary incontinence and skin wrinkles, the microspheres may also be used with anti-inflammatory agents, angiogenesis inhibitors, radioactive elements, and antimitotic agents.

Other therapeutic agents to be used in combination with the microspheres or microparticles of the present invention include those for the treatment of skin disorders, GERD and urinary incontinence as reported in Goodman & Gilman's The Pharmacological Basis of Therapeutics, 9th Ed., McGraw-Hill (1996) and The Physicians's Desk Reference® 1997.

The primary advantages of the method of treating GERD according to the present invention over the prior art methods are:

a) Less invasive effects on the patient compared to surgery;
b) More permanent effects over antacids or other drugs;
c) Good biocompatibility with chemotactic effects; and
d) Ability to use X-ray visualization or MRI to assist in follow-up evaluation of the patient.

For the treatment of urinary incontinence, the microparticles, or other solid substrates, are introduced via the urethra and injected into the walls of the bladder sphincter, decreasing the internal lumen of the sphincter muscle thus permitting easier contraction of the muscle with reduced likelihood of incontinence. The microparticles, or other solid substrate, may also be loaded with X-ray opaque dye, or other imaging agents for subsequent X-ray visualization.

In another embodiment, microparticles injected into the bladder sphincter in order to treat urinary incontinence may also include an amount of a drug used to treat urinary incontinence, such as antidiuretics, anticholinergics, oxybutynin and vasopressins.

Injected microparticles can generate some transient adverse reactions such as local inflammation, therefore the microparticles can contain or be injected with anti-inflammatory drugs, such as salicylic acid derivatives including aspirin; para-aminophenol derivatives including acetaminophen; non-steroidal anti-inflammatory agents including indomethacin, sulindac, etodolac, tolmetin, diclodfenac, ketorolac, ibuprofen, naproxen, flurbiprofen, ketoprofen, fenoprofen, oxaprozin; anthranilic acids including mefenamic acid, meclofenamic acid; enolic acids such as piroxicam, tenoxicam, phenylbutazone, oxyphenthatrarone; and nabumetone. These anti-inflammatories are preferably adsorbed on the microparticle's network and released slowly over a short period of time (a few days). The microparticles may also be used to release other specific drugs which can be incorporated within the microparticle network before injection into the patient. The drug would be released locally at the site of implantation over a short period of time to improve the overall treatment.

Incorporation of active molecules, such as drugs, into the microparticles of the present invention can be accomplished by mixing dry microparticles with solutions of said active molecules or drugs in an aqueous or hydro-organic solution. The microparticles swell by adsorbing the solutions and incorporate the active molecule of interest into the microparticle network. The active molecules will remain inside the microparticle due to an active mechanism of adsorption essentially based on ion exchange effect. The microparticles by their nature carry cationic groups and have the ability to adsorb anionic molecules, such as well known anti-inflammatory drugs, and these anionic molecules are then released slowly upon injection into the patient due to the action of physiological salt and pH. The ability of various types of microparticles to adsorb drug molecules may be readily determined by the skilled artisan, and is dependent on the amount of cationic monomers present in the initial solution from which the microparticles are prepared.

Some of the primary advantages of treating urinary incontinence according to the present invention over prior art methods are:

a) More permanent effect than the use of regular viscous solutions of collagen;

b) Good biocompatibility with chemotactic effect;

c) Visualization under X-ray or MRI to assist in follow-up evaluation; and d) Preventing repeated treatments with resorbable naturally occurring substances like collagen.

The primary advantages of the method of treating skin wrinkles according to the present invention are:

(a) less invasive effects on the patient compared to surgery;

(b) more permanent effects than the use of collagen injections; and (c) good biocompatibility with chemotactic effects.

For treatment of skin wrinkles, the microparticles may be introduced via injection. The microparticles may also include one or more anti-inflammatory agents.

The invention is further defined by reference to the following examples that describe in detail the preparation of microparticles for use in tissue bulking, and the treatment of skin wrinkles, urinary incontinence, and GERD. The following examples are illustrative only and should in no way limit the scope of the present invention. It will be apparent to those skilled in the art that many modifications, both to materials and methods, may be practiced without departing from the purpose and scope of this invention.

6. EXAMPLES

6.1 Example 1

Preparation of Irregular Hydrogel Particles with Chemotactic Properties 58 grams of sodium chloride and 27 grams of sodium acetate were dissolved at room temperature in 100 ml of demineralized water. To this solution 400 ml of glycerol were added, the pH was adjusted to 6.0 and monomers were then dissolved. More specifically to this solution 90 gram of methylolacrylamide, 2 g of methacrylamidopropyl-trimethyl-ammonium-chloride hydrochloride and 10 gram of N,N'-methylene-bis-acrylamide were added and the mixture was agitated until complete solubilization. The solution was heated at about 70° C. and 100 ml of a solution of gelatin at a concentration of 500 mg/ml was added. The total volume of the mixture was then adjusted to 1000 ml by addition of demineralized water. Finally 20 ml of 70 mg/ml ammonium persulfate aqueous solution and 4 ml of N,N,N',N'-tetramethyl-ethylene-diamine was added. The obtained mixture was stored at 70° C. for about 3 hours until formation of a compact three-dimensional gel. This gel was totally insoluble in water. It was cut in small pieces and then ground to get very small particles of a dimension close to 100–200 $\mu$m. The particles were then suspended in 1 liter of physiological buffer containing 5% (w/v) glutaraldehyde and were shaken for two hours. Finally the particles were extensively washed to eliminate unpolymerized material, by-products and salts. To obtain homogeneous particle size distribution the particle suspension was sieved using an appropriate sieving net.

These particles possess the characteristics desired for tissue cell adhesion prior to muscle bulking and include cationic groups and adhesion agents for an effective cell adhesion mechanism.

6.2 Example 2

Preparation of Spherical Polyacrylic Hydrogel Gel Particles with Chemotactic Properties The solution of monomers prepared as described in Example 1 above was poured slowly into 1500 ml of stirred and hot paraffin oil (50–70° C.). After a few minutes a suspension/emulsion of liquids was obtained (the aqueous monomer solution was dispersed into oil and forms very small spherical droplets) and the polymerization occurred in suspension. The microdroplets were transformed into microbeads. The solid microbeads were recovered by centrifugation and suspended in 1 liter of physiological buffer containing 5% (w/v) glutaraldehyde and shaken for two hours. Finally the particles were extensively washed with water to eliminate completely the oil traces. Organic solvent extraction can be used for a more effective oil removal or an extensive washing in the presence of traces of nonionic detergents. The obtained microbeads are calibrated if necessary by sieving through a nylon net and sterilized in an autoclave. These microspheres possess desired characteristics and properties for cell adhesion prior to muscle bulking.

6.3 Example 3

Preparation of Hydrophilic Spherical Polystyrene Copolymer Particles Useful for Tissue Bulking 10 gram of styrene is mixed with 60 ml of toluene. 1 gram of divinylbenzene, 1 gram of dimethyl-aminoethyl-methacrylate and 1 gram of dimethyl-acrylamide are added to the resulting solution. After complete solubilization the monomer solution is mixed with 1% of AIBN (2,2'-azobisisobutyronitrile) as a polymerization catalyst and with 40 ml of paraffin oil as a viscosity inducer agent. The mixture is poured in an agitated water solution containing 0.5% Tween 80. In this situation there is formation of droplet suspension which turns into solid microbeads when the temperature is raised to 80–90° C. for three to five hours. The resulting beads are dried and organic solvents extracted. They are then swollen in an aqueous solution of collagen in phosphate buffer at neutral pH. Embedded collagen is then crosslinked with glutaraldehyde as described in Examples 1

6.4 Example 4

Preparation of Hydrophilic Silicone Beads for Cell Adhesion and Tissue Bulking and 2. The resulting beads possess cationic charges to interact with cell tissues and collagen for cell adhesion, and a chemotactic agent for cell growth and biocompatibility. They are suitable as tissue bulking agent.

10 gram of silicone beads of a diameter of 20–300 μm are suspended in 30 ml of a solution of hexadecylamine (10 mg/ml) in ethylacetate. The suspension is stirred for two hours and 100 ml of ethanol is added. A 1 M ammonium sulfate or sodium chloride solution in water is added slowly until a 300 ml suspension is obtained. The amino-containing silicone beads are then reacted with a butanedioldiglycydylether in alkaline conditions. Epoxy derivatives are thus obtained on which gelatin is coupled using a method well known in the art. The resulting beads have the target properties of biocompatibility, hydrophilicity, non-biodegradability and cell adhesion by the presence of cationic amino groups and of gelatin as a cell growth promoting agent. They are suitable for tissue bulking in accordance with the present invention.

6.5 Example 5

Preparation of Beads for Tissue Bulking Containing Adhesion Factors

Beads prepared according to Example 2 were chemically activated with well known reagents used in the preparation of affinity chromatography sorbents. Activated beads were then used for the immobilization of cell adhesion agents such as fibronectin or vitronectin or laminin. Adhesion agents were dissolved at 1–10 mg/ml in a coupling buffer (100 mM carbonate or borate buffer pH 8 to 10) and the solution was mixed with the activated beads. The resulting beads possess the target properties of cell adhesion and growth, non-biodegradability and were non-resorbable. They are suitable for cell adhesion and permanent tissue bulking in accordance with the present invention. Similarly, beads prepared according to Examples 3 and 4 can also be used.

6.6 Example 6

Preparation of Spherical Polyacrylic Hydrogel Particles with Chemotactic Properties Microbeads commercially available under the name SPEC-70 (BioSepra Inc., Marlborough, Mass.) are polyacrylic polyanionic beads with elastic properties suitable for tissue bulking applications. However, these microbeads are not chemotactic and do not possess cationic charges. SPEC-70 microbeads are first drained under vacuum to eliminate water and then suspended in an aqueous solution of 1% chondroitin sulfate sodium salt in physiological conditions. Once this compound is absorbed on the bead structure, the beads are drained under vacuum and suspended in an aqueous solution containing 20% polylysine by weight. The suspension is shaken for a few hours and then drained under vacuum and rapidly washed with distilled water. The beads are then suspended in a solution of 5% butanedioldiglycidylether in ethanol and shaken overnight. Under these conditions, the polylysine is crosslinked as well as chondroitin sulfate. The resulting modified beads possess properties such as cationic charge for cell adhesion and promoting agents for cell growth such as polylysine and chondroitin sulfate.

6.7 Example 7

Preparation of Radiopaque Microbeads with Chemotactic Properties for Tissue Bulking Microbeads from Examples 2 were drained under vacuum and then suspended in a saturated solution of barium chloride. They were shaken for two hours at room temperature and then drained under vacuum to eliminate the excess of barium chloride solution. The beads were suspended in a saturated solution of ammonium sulfate and shaken for two additional hours before elimination of the excess ammonium sulfate by vacuum filtration. This operation of contact with barium salts and ammonium sulfate can be repeated several times until the resulting radiopaque precipitate inside the beads reaches the desired amount. Resulting beads have radiopaque properties without having lost their initial desirable properties for tissue bulking. The microbeads from Examples 3, 4 and 6 can be similarly used.

6.8 Example 8

Preparation of Radiopaque Microbeads with Chemotactic Properties for Tissue Bulking Microbeads from Example 6 coated with polylysine are washed extensively with distilled water and suspended in a solution of sodium triazoate. The suspension pH is adjusted at about 7 by addition of acetic acid and shaken for several hours. The triazoate which is a radiopaque molecule is adsorbed tightly to the beads and the remaining reagents are eliminated by washing under vacuum. The resulting beads still possess cell promotion properties and now radiopacity as well.

6.9 Example 9

Introduction of Anti-inflammatory Drugs Inside the Bulking Beads

Microbeads described in the previous Examples may generate local temporary inflammatory reactions when injected in the target tissue. To avoid or decrease this phenomenon, the microbeads once coated with autologous cells can be filled with one or more anti-inflammatory drugs. The microbeads are cationic by their nature and can absorb anionic drugs by ion exchange effect.

Prior to injection microbeads are mixed with a 10 mg/ml anti-inflammatory anionic drug solution in sterile physiological saline. The suspension is shaken for several hours, and the beads filled with the drug are recovered by filtration or centrifugation. The resulting anti-inflammatory containing microbeads may then be used as tissue bulking agents for use in the present invention.

6.10 Example 10

In Vitro Pre-adipocytes Adhesion and Growth on Polymeric Beads

In order to assess the ability of polymeric beads from Example 2 to allow adhesion and growth of pre-adipocytes, fresh pre-adipocytes were collected and isolated from Wistar rat peri-epididymal fat tissue. Pre-adipocytes were then cultured in the presence of above described microbeads at a concentration of about $7.1 \times 10^5$ to about $1.7 \times 10^6$ cells/ml using the classical protocol for microcarrier culture in vitro. In a first phase the cells adhere on the bead surface and then they grow to totally cover the bead surface. The total colonization period is about 72 hours.

Pre-adipocytes from this type of culture show good growth and specific biological activity associated with differentiation into adipocytes (accumulation of lipids). Moreover these cells show the presence of specific enzymatic markers such as glycerol-3-phosphate-dehydrogenase and malate dehydrogenase. Microbeads having cells adhered thereto are useful for tissue bulking for use in the present invention. The polymeric beads of Examples 2 to 5 can be similarly assessed.

6.11 Example 11

Culture of Pre-adipocytes and Myocytes on Microbeads In Vitro to Check Their Ability of Integrate Into an In Vivo Tissue Preadipocytes and smooth muscle cells were isolated from Wistar rats according to a classical protocol to eliminate most of other contaminating cells. Separately these cells were cultured in a Petri dish in the presence of Dulbecco's Modified Eagle Medium supplemented with 10% fetal bovine serum. Gelatin-coated cationic microbeads prepared in accordance with Example 2 were added to cells cultured in vitro until they covered the surface of the Petri dish. Initial cell seed concentration was $0.7 \times 10^6$ cells/ml.

Repeated observations showed that cells adhered on the surface of microbeads and further multiplied to cover all the surface of the beads. After 5 to 7 days of culturing, there was formation of a solid network of beads where cells acted as a binder to consolidate the blocks of several beads. In most cases there were formation of solid non dissociable aggregates comprising beads and cells.

When, after a growing period (generally 5 to 7 days), a differentiating element such as 3,3',5-triiodo-D-thyronine was added to preadipocytes, the preadipocytes started to accumulate fats as micro-droplets within the cytoplasm.

Specific staining with 3,3'-dioctadecyloxacarbocyanine perchlorate or 2'-[4-hydroxyphenyl]-5-[4-methyl-1-piperazinyl]2,5'-bi-1H-benzimidazole demonstrated good adhesion of the cells on the bead substrate.

Staining of the cells with red oil at the beginning of the differentiating phase evidenced the accumulation of fats inside the cells.

In addition, specific enzymatic reactions of malic enzyme indicated that, at the end of the culture, resulting adipocytes were functionally viable with their major expressed characteristics. This enzyme is not expressed at the beginning of the culture and appeared simultaneously with the accumulation of fats.

Smooth muscle cells were also followed in their proliferation by DNA synthesis assay; their adhesion on the substrate was followed as per preadipocyte cells. Myocytes also showed good proliferation as well as adhesion on the beads.

6.12 Example 12

In vitro Myocyte Adhesion and Growth on Polymeric Beads

In order to assess the ability of polymeric beads from Example 2 to allow adhesion and growth of muscle cells, fresh smooth cell myocytes were collected from rat esophagus according to classical procedures. Cells were then cultured in the presence of above described microbeads at a concentration of about $10^6$ cells/ml using the classical protocol for microcarrier culture in vitro. In a first phase the cells adhered on the bead surface and then they grow until they cover the total bead surface. The total colonization period was about 72 hours.

Myocytes from this type of culture showed good growth and behavior and displayed the specific myosin marker. These microbeads having cells adhered thereto are useful for tissue bulking in accordance with the present invention. The beads from Examples 2 to 5 can be similarly assessed.

6.13 Example 13

Preparation of Injectable Suspension of Cell-microbead Particles for In Vivo Bulking At the issue of cell culture phase, the cell-bead particles are collected by filtration and washed extensively with blood serum from the host where the material is to be implanted. This operation ensures the elimination of foreign material from cell culture. The microbeads are then suspended in a few ml of autologous serum (a ratio of beads/serum is about 1:1) and are ready to be injected within the tissue to be bulked by means of an appropriate syringe or other injection device.

6.14 Example 14: Preparation of Injectable Suspension of Cell-microbeads Particles for In Vivo Bulking Microbeads described in Example 2 are colonized with rat muscle cells according to Example 10 and conditioned according to Example 13 using rat serum diluted with physiological saline (50%-50%). The final sterile suspension of cells anchored on beads (50% of volume is constituted of beads and 50% of physiological saline) is injected in the right thigh muscle of a rat. Three months after bead injection the muscle was observed in its shape and histologically examined. Muscle volume should be larger than the left thigh muscle upon autopsy. Beads inside the muscle mass should appear surrounded by fibroblastic cells with no specific adverse inflammatory or necrosis effects.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference.

Other embodiments are within the following claims.

What is claimed is:

1. A method for treating urinary incontinence which comprises administering to a mammal in need of such treatment a therapeutically effective amount of biocompatible cationic hydrophilic flexible microparticles comprising a positive charge on their surface, said administration into the bladder sphincter.

2. The method of claim 1 wherein said mammal is a human.

3. The method of claim 1 wherein the microparticles are pre-treated with, administered with or coated with autologous cells.

4. The method of claim 1 wherein the microparticles are washed with serum or whole blood prior to administration.

5. The method of claim 3 wherein the microparticles are washed with serum or whole blood prior to administration.

6. The method of claim 3 wherein the autologous cells are bladder cells, muscle cells, fat cells or combinations thereof.

7. The method of claim 1 wherein the microparticles are coated with or covalently linked to at least one of collagen or a derivative thereof, glucosaminoglycan, or a mixture thereof.

8. The method of claim 1 wherein the microparticles are administered in a sterile and pyrogen-free injectable solution.

9. The method of claim 1 wherein said administration is made via syringe.

10. The method of claim 1 wherein said microparticles are spherical.

11. The method of claim 10 wherein said microparticles comprise a hydrophilic copolymer which comprises in copolymerized form about 25 to about 99% by weight of neutral hydrophilic acrylic monomer, about 2 to about 50% by weight of one or more monomers having a cationic charge, and about 1 to about 30% by weight of a functionalized monomer.

12. The method of claim 1 wherein said microparticles are loaded with or administered with one or more anti-inflammatory agents.

13. The method of claim 11 wherein said microparticles have a diameter ranging between about 10 to about 1000 μm.

14. A method for treating urinary incontinence disease comprising:

(a) preparing cationic flexible microparticles which comprises hydrophilic polymers;

(b) administering the resulting microparticles to a mammal through the urethra and injecting the microparticles into walls of the bladder sphincter.

15. The method of claim 11, wherein the microparticles further comprise a cell adhesion promoter.

16. The method of claim 11, wherein the microparticles further comprise a cell adhesion promoter.

17. The method of claim 14, wherein the microparticles further comprise a cell adhesion promoter.

18. The method of claim 1, wherein the microparticles are administered with a therapeutic agent.

19. The method of claim 18, wherein the therapeutic agent is selected from the group consisting of antidiuretics, anticholinergics, oxybutynin and vasopressins.

20. The method of claim 1, wherein the microparticles are administered with one or more of an anti-inflammatory agent, an angiogenesis inhibitor, a radioactive element, and an antimitotic agent.

21. The method of claim 1, wherein the microspheres further comprise one or more of a therapeutic agent, an anti-inflammatory agent, an angiogenesis inhibitor, a radioactive element, and an antimitotic agent.

* * * * *